United States Patent [19]

Nelson

[11] 4,028,057
[45] June 7, 1977

[54] GAS ANALYZER

[75] Inventor: David M. Nelson, Verona, Pa.

[73] Assignee: Ambac Industries, Inc., Pittsburgh, Pa.

[22] Filed: Apr. 29, 1976

[21] Appl. No.: 681,444

[52] U.S. Cl. .............................. 23/254 E; 340/180; 340/188 R; 340/212; 340/285

[51] Int. Cl.² .................. G01N 27/16; G08B 21/00

[58] Field of Search .......... 23/254 E, 255 E, 232 E; 340/180, 188 R, 212, 285

[56] References Cited

UNITED STATES PATENTS

| 2,899,281 | 8/1959 | Olmer | 23/254 E |
| 3,586,486 | 6/1971 | Kim et al. | 23/254 E |
| 3,877,291 | 4/1975 | Hoppesch et al. | 23/254 E X |
| 3,943,766 | 3/1976 | Delany | 23/254 E X |

Primary Examiner—Joseph Scovronek
Attorney, Agent, or Firm—Parmelee, Miller, Welsh & Kratz

[57] ABSTRACT

A gas analyzer in which a catalytic resistance element creates an imbalance in a Wheatstone bridge and lights a number of successive light emitting diodes arranged in a color coded analog display which is rugged, stable and easily read under all light conditions, in proportion to the subject gas present. Erratic and confusing indications are eliminated by driving the bridge into negative imbalance during the warm-up period. Initial warm-up, testing of the battery and transition to the monitor function is accomplished by a single operating stroke of only one switch.

4 Claims, 2 Drawing Figures

GAS ANALYZER

BACKGROUND OF THE INVENTION

1. Field of the Invention

This invention relates to gas analyzers of the type in which the impedance of an active element varies in the presence of the subject gas and creates an imbalance in a Wheatstone bridge measuring circuit.

2. Prior Art

Gas analyzers of the Wheatstone bridge type are well known. Some utilize a simple thermal detector while others, now more common, employ an electrically heated catalytic resistance element which actually initiates combustion of the gas. In either case the presence of the gas changes the impedance of the active element which creates an imbalance in a Wheatstone bridge measuring circuit, the magnitude of which is an indication of the percentage of the subject gas present. An example of a typical prior art analyzer is disclosed in U.S. Pat. No. 3,586,486 which has been assigned to the assignee of this invention. In analyzers of this general type, a noncatalytic compensating resistance element is placed in an adjacent leg of the Wheatstone bridge to counteract the effect of ambient conditions on the active element. While this patent describes a construction in which a constant flow of a predetermined mixture of the gas to be analyzed and a dilutant gas is drawn across the resistive elements, other analyzers expose the resistive elements directly to the atmosphere to be tested through porous flame suppressors.

Prior art analyzers employ either electro-mechanical meters or, more recently, digital readouts for displaying the gas concentration. Mechanical type movements have always been susceptible to breakage which is a serious handicap for use in rugged environments, such as mines. Mechanical meters are also subject to operator interpretation which can lead to errors in reading especially under poor lighting conditions unless adequate internal lighting is provided which increases the current draw on the batteries of a portable analyzer. Furthermore, some mechanical displays which appear to provide large full-scale indications are difficult to read in the lower more commonly used ranges and are therefore subject to even more interpretation.

On the other hand, digital type displays have failure modes which can be dangerous for applications such as the detection of methane gas in coal mines where a concentration of 2 percent or more is unsafe. For instance, failure of one segment in a digital reading of "1.8" percent can be displayed as "1.0" percent which would give the false impression that the concentration of methane was at a safe level when in fact it was approaching a critical level. In addition, digital displays draw close to maximum current while indicating zero percent by displaying 0.0 percent which requires the energization of 12 segments on the conventional digital display. Since the absence of methane gas is a common and strived for occurrence in coal mines, displays which draw maximum current at a zero reading are not as desirable as one which would draw minimum current in the most common operating range. Furthermore, some digital displays are confusing in that they can display negative numbers such as −1.8 percent.

Some electro-mechanical meters and digital displays have a tendency to show annoying fluctuation. They may also display erratic false readings during the warm-up of the resistance elements. In addition, many of the prior art analyzers require the operation of separate switches to test the battery and to take readings.

Light emitting diodes (LEDs) are now widely used in digital displays. There has also been a suggestion that LEDs could be arranged to provide an analog display of the speed of a vehicle.

SUMMARY OF THE INVENTION

According to the invention a gas analyzer having catalytic and compensating resistance elements in a Wheatstone bridge measuring circuit, has an electric power supply connected across the Wheatstone bridge, a plurality of light emitting diodes (LEDs) arranged to form an analog display; and means for applying electric power from the power supply to a number of successive LEDs in the analog display in proportion to the imbalance of the Wheatstone bridge and therefore in proportion to the percentage of the subject gas present in the atmosphere adjacent the catalytic resistance element. In the preferred embodiment, the LEDs are arranged in a line with those representative of predetermined acceptable levels of concentration of the subject gas radiating a first color light and those associated with higher concentrations of the gas radiating a second color light. Preferably, the LED associated with the highest displayable level of concentration of the gas is separated from the other LEDs so that saturation of the analyzer can easily be observed at a glance.

The analyzer includes a reference voltage generator for generating a plurality of voltages ranging in magnitude in steps from a voltage corresponding to a balanced output of the bridge up to a voltage corresponding to a predetermined imbalance and comparison means associated with each LED in the analog display for comparing the output of the Wheatstone bridge with one of said plurality of reference voltages and for turning on the associated LED when the output of the bridge circuit exceeds the associated reference voltage.

Another aspect of the invention takes advantage of the fact that the resistance of both the catalytic and compensating resistance elements increases as they are heated by the electric current flowing through the bridge circuit. According to this aspect of the invention, an impedance which is relatively temperature independent compared to the catalytic and compensating resistance elements is placed in parallel with the compensating resistance element in one leg of the Wheatstone bridge circuit such that the output of the bridge circuit is driven negative until the resistance elements reach operational temperature. This prevents erratic and erroneous readings during the warm-up period by keeping the LEDs turned off.

Preferably, the analyzer is powered by a battery through a voltage regulator. An additional LED which is energized when the voltage produced by the voltage regulator is above the threshold of the additional LED serves as a battery tester. The additional LED is shunted by an electronic switch which is controlled by a control element connected with the light emitting diode associated with a balanced condition of the Wheatstone bridge. When the resistance elements have warmed up and the light emitting diode is turned on, the electronic switch is also turned on to short circuit and thereby turn off the additional LED.

As still another aspect of the invention, a single switch is provided which through a single operating stroke applies electric power of the Wheatstone bridge circuit to initiate heating of the resistance elements and to the additional light emitting diode to indicate acceptable supply voltage until the resistance elements reach operational temperature whereupon the LED associated with a balanced Wheatstone bridge circuit illuminates and turns off the additional LED and a number of successive LEDs in the analog display are illuminated in proportion to the amount of the subject gas present adjacent the catalytic resistance element.

A gas analyzer constructed in accordance with the teachings of this invention is rugged, compact and has a stable display which is quickly and easily read in all lighting conditions. The analog display is easily interpreted and the color coding provides an instant indication of the safety of the concentration of gas being detected. The separation between the LED representing the highest displayed level of concentration and the other LEDs in the analog display further gives an instant indication of an over range condition. In addition, the device has no dangerous failure modes in that if one of the LEDs or its associated circuitry fails, the maximum error for the embodiment specifically disclosed will be 0.2 percent unlike the digital display which, as discussed above, can be as much as 0.8 percent off in a particular failure mode.

Another advantage of the device is that it has no moving parts other than the switch and therefore it is not as subject to mechanical shocks as the mechanical meter. Finally, it is easy to use since one merely presses and holds a single button and warm-up, testing of the battery and transition to metering is all accomplished automatically.

DESCRIPTION OF THE PREFERRED EMBODIMENT

Figure 1:
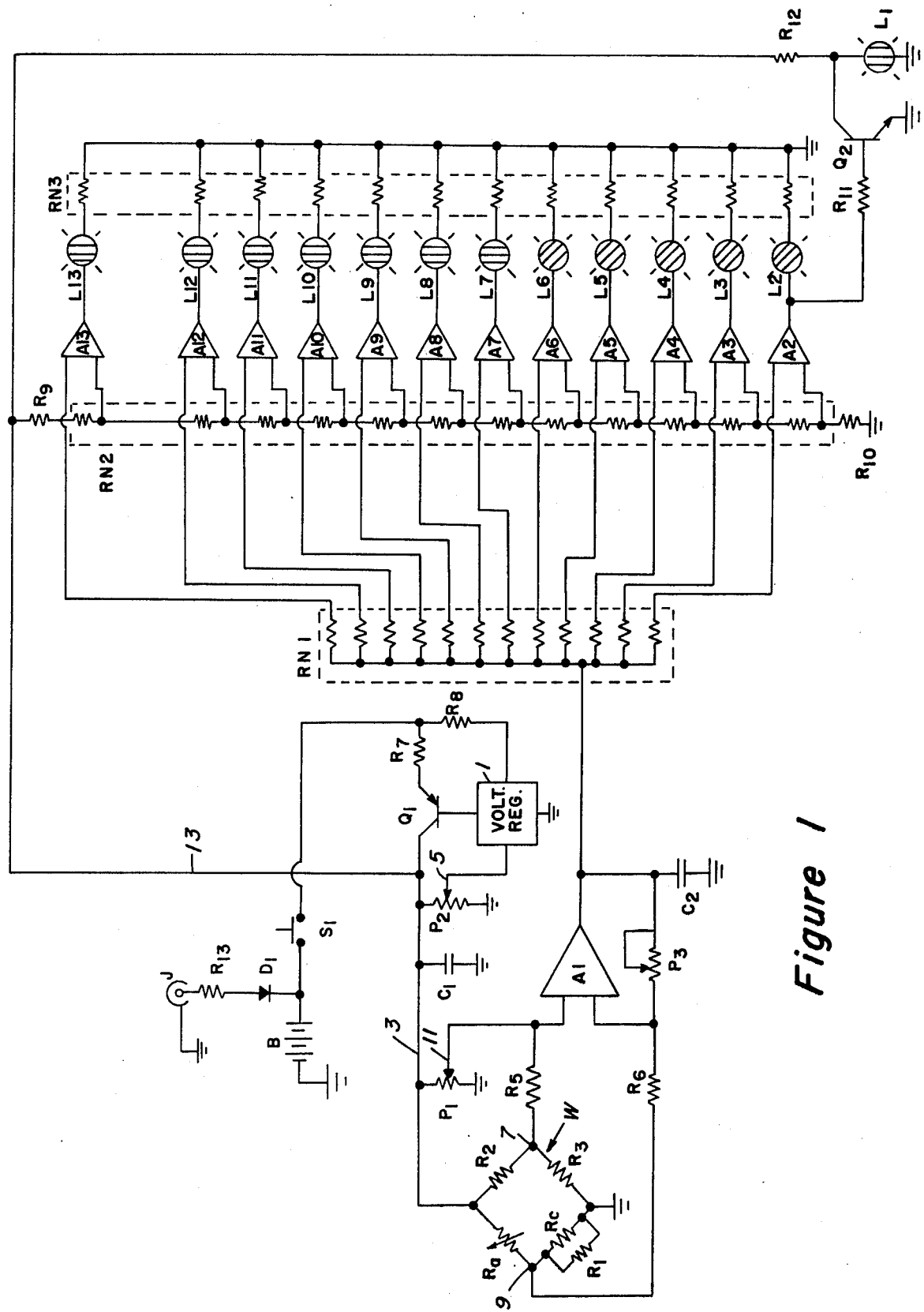
FIG. 1 is a schematic circuit diagram of a gas analyzer according to the invention.

FIG. 1 discloses a schematic circuit diagram for a gas analyzer in which a catalytic resistance element $R_A$ and a compensating resistance element $R_C$ similar to the element $R_A$ but without the catalyst are connected in adjacent legs of a grounded Wheatstone bridge measuring circuit W together with resistors $R_2$ and $R_3$. An additional resistor $R_1$ is connected in parallel with the compensating resistance element $R_C$ for reasons to be discussed below. It is well known that the presence of the catalyst in the electrically heated catalytic resistance element initiates combustion of the detected gas which raises the resistance of the active element and affects the balance of the Wheatstone bridge. The catalytic resistance element is chosen for its selectivity in initiating combustion of the desired gas. Catalytic resistance elements responsive to all known combustable gases are available. For the purposes of this disclosure, a methane detector using platinum as the catalyst will be described but it is to be understood that the teachings herein are applicable to the detection of other combustible gases and to detectors utilizing other catalysts.

Electric power for the meter is provided by a 6 volt nickel cadmium battery B, the negative terminal of which is grounded. The battery may be recharged as necessary from jack J through resistor $R_{13}$ and diode $D_1$. The diode $D_1$ prevents discharge of the battery through the jack J and thereby eliminates the danger of ignition of methane gas through arcing at the jack. Current from the battery is applied to a voltage regulator 1 through a switch $S_1$ and resistor $R_8$. The voltage regulator 1 controls the base bias of a pass element in the form of p-n-p transistor $Q_1$. The emitter of transistor $Q_1$ is connected to the battery through resistor $R_7$ and the switch $S_1$. The collector of $Q_1$ supplies current to the Wheatstone bridge W through lead 3 at a voltage determined by the voltage regulator 1. The position of the slider 5 on potentiometer $P_2$ connected between lead 3 and ground determines the voltage output of the regulator 1. A filter capacitor $C_1$ is also connected between lead 3 and ground.

The output terminals 7 and 9 of the Wheatstone bridge W are connected to the inputs of an amplifier $A_1$ through resistors $R_5$ and $R_6$ respectively. The slider 11 of a potentiometer $P_1$, also connected between lead 3 and ground, provides a zero adjustment for the bridge circuit through application of a bias voltage to one input of the amplifier $A_1$. Another potentiometer $P_3$, connected as a variable resistor between the output and the second input of the amplifier $A_1$, provides a span adjustment for the output signal. A capacitor $C_2$ connected between the output of amplifier $A_1$ and ground averages the output signal for a more stable response.

The filtered output signal of amplifier $A_1$ is applied to a branching resistor network $RN_1$ containing 12 resistors of equal value. Each resistor of network $RN_1$ is connected to one input of an associated operational amplifier $A_2$ through $A_{13}$. A second input of each operational amplifier $A_2$ through $A_{13}$ is connected to an associated output of a second resistor network $RN_2$. Network $RN_2$ comprises a number of series connected resistors of equal value with intermediate tap points. A lead 13 supplies a regulated voltage to network $RN_2$ through resistor $R_9$. The other end of the network $RN_2$ is connected to ground through resistor $R_{10}$. Network $RN_2$ therefore forms a voltage generator which generates a plurality of voltages which increase incrementally in magnitude.

The outputs of operational amplifiers $A_2$ through $A_{13}$ are connected to light emitting diodes (LEDs) $L_2$ through $L_{13}$ respectively. Each LED $L_2$ through $L_{13}$ is also connected to ground through an associated resistor of branching resistor network $RN_3$. An additional LED $L_1$ is energized by lead 13 through resistor $R_{12}$ and ground. An electronic switch in the form of n-p-n transistor $Q_2$ is connected between the hot side of LED $L_1$ and ground. The base $Q_2$ is connected to the output of operational amplifier $A_2$ through resistor $R_{11}$.

The circuit of FIG. 1 operates in the following manner. When the switch $S_1$ is closed, the voltage regulator 1 controls the conductivity of transistor $Q_1$ to generate a voltage on leads 3 and 13 as determined by the setting of potentiometer $P_2$. In the exemplary circuit, this voltage is set at approximately 4 volts. This voltage on lead 13 is sufficient to turn on LED $L_1$ indicating that sufficient voltage is available from the battery. LEDs have a rather sharp threshold and by appropriately selecting the value of resistor $R_{12}$ it can be arranged that LED $L_1$ will not light if the voltage on lead 13 does not exceed a predetermined value. Hence the illumination of $L_1$ when the switch $S_1$ is first depressed is an indication of adequate battery power to operate the meter.

At the same time the voltage on lead 3 is applied to the Wheatstone bridge W to initiate warm-up of the catalytic and compensating resistance elements $R_A$ and $R_C$ respectively. Since the resistance of these elements remains below the normal operating value during warm-up, the resistor $R_1$, which in the exemplary circuits is a 10 ohm resistor, unbalances the bridge circuit to produce a negative input to amplifier $A_1$. The negative output of amplifier $A_1$ is applied to the first input of each operational amplifier $A_2$ to $A_{13}$ through resistor network $RN_1$.

When connected as described, the operational amplifiers $A_2$ through $A_{13}$ serve as comparison means which generate zero output when the voltage applied to the first input through network $RN_1$ is less than the voltage produced at the second input by the associated output of resistor network $RN_2$. On the other hand, when the voltage applied to one of the operational amplifiers by network $RN_1$ exceeds the voltage applied by the associated output of network $RN_2$, the amplifier generates an output which turns on the associated LED. Thus during the warm-up period when the output of amplifier $A_1$ is negative, all of the LEDs $L_2$ through $L_{13}$ will be turned off. $L_1$, however, as mentioned, will be turned on to indicate that the battery is supplying sufficient power to operate the circuits discussed above.

As the catalytic and compensating resistance elements $R_A$ and $R_C$ reach operating temperature, the Wheatstone bridge will reach a balanced state assuming that there is no methane present in the ambient air. With the bridge in the balanced state the bias generated by the "zero" potentiometer $P_1$ is sufficient to generate a voltage at the output of the amplifier $A_1$ which generates a first input to operational amplifier $A_2$ which exceeds the voltage applied to the second input by network $RN_2$ but does not exceed the second input to any of the other operational amplifiers $A_3$ through $A_{13}$. This turns on LED $L_2$ and also turns on transistor $Q_2$ which turns off LED $L_1$.

If methane is present in the ambient air, the catalytic resistance element causes combustion of the gas which heats the catalytic element further and raises its resistance in proportion to the percentage of methane present. A porous fire suppressor, as used in the prior art (not shown), placed over the catalytic resistance element prevents ignition of the gas other than that adjacent the catalytic element. This increase in resistance of the catalytic element unbalances the bridge to generate a positive input to the amplifier $A_1$, the magnitude of which is a function of the proportion of methane present. The output of amplifier $A_1$ will apply an input to a number of successive ones of the operational amplifiers $A_3$ through $A_{13}$ which exceeds the associated second input from the resistor network $RN_2$, again in proportion to the amount of methane present. Thus a proportionate number of the LEDs $L_2$ through $L_{13}$ will be turned on to give a visual display of the percentage of methane in the sample.

Figure 2:
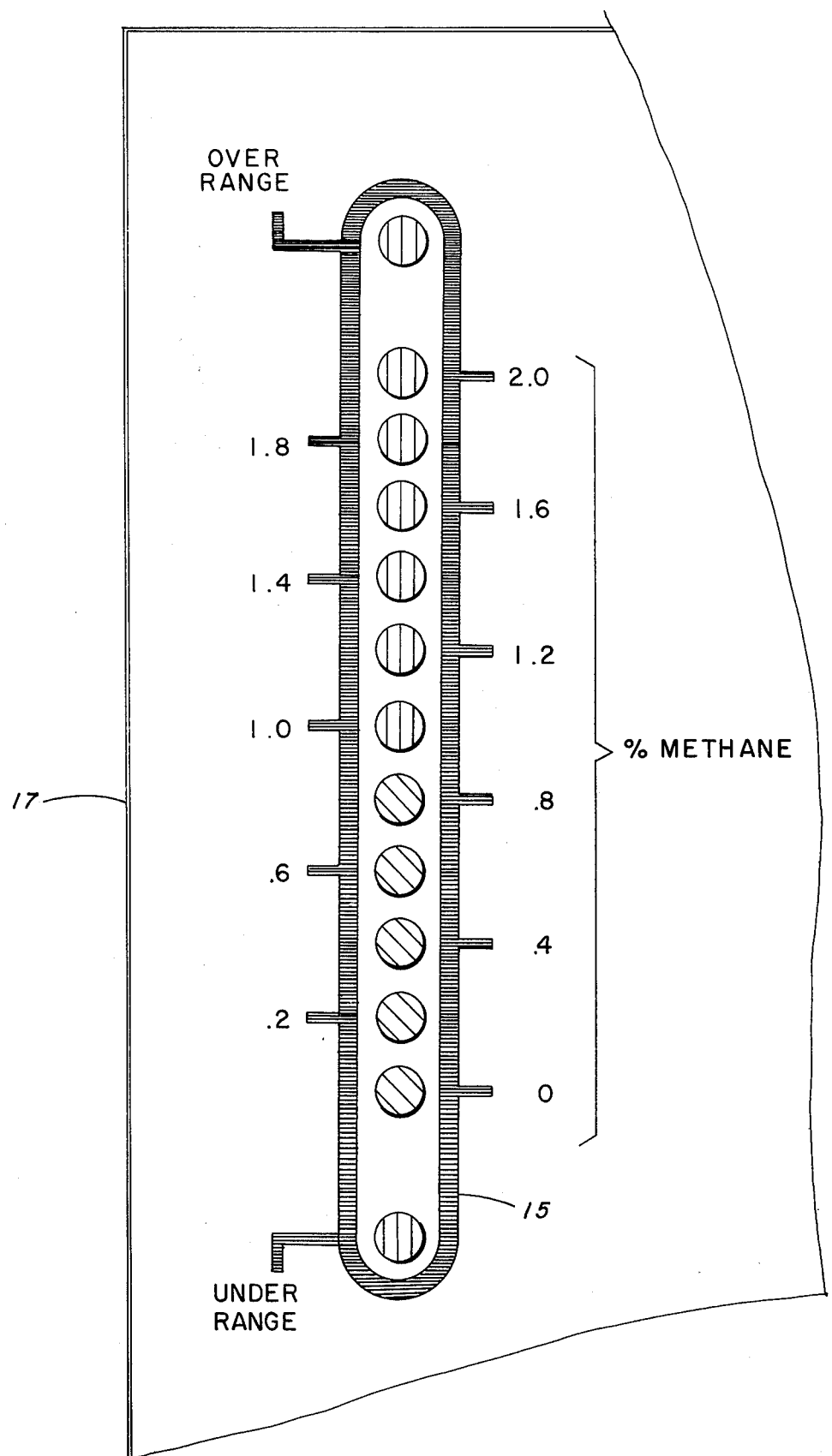
FIG. 2 is a plan view of an analog display for the gas analyzer of FIG. 1.

FIG. 2 illustrates the preferred form of the display. The LEDs are arranged in a straight line along a cutout 15 in a face plate 7 such that the length of the line generated by the illuminated LEDs is an indication of the methane concentration in the sample. In this display, the LED opposite the "UNDER RANGE" legend is $L_1$, $L_2$ is opposite the "0" legend and so on to $L_{13}$ which is opposite the "OVER range" legend on the face plate. As indicated by the shading, the "UNDER RANGE" LED and the LEDs associated with "1.0" percent upward through the "OVER RANGE" LED are red. The LEDs associated with "0" percent through ".8" are green.

Thus during the warm-up period, $L_1$ opposite the "UNDER RANGE" indication will illuminate red to indicate that sufficient power is available to operate the meter but that it has not yet warmed-up. When the catalytic and compensating elements have warmed-up the "0" LED will turn on and the "UNDER RANGE" LED will go out. Assuming that there is no methane present, the "0" LED alone will remain illuminated as long as switch $S_1$ is held depressed. If there is methane present, additional LEDs in succession will be illuminated. As long as the methane concentration does not rise above 0.8 percent, only green LEDs will illuminate. If the concentration exceeds 0.8 percent, the appropriate number of red LEDs in addition to all the green LEDs will be turned on. When the concentration of methane exceeds 2 percent, the LED opposite the "OVER RANGE" legend will illuminate.

The described display is easy to read even if there is not enough light to read the legend on the face plate. If no lights appear when the switch $S_1$ is pressed, not enough battery power is available to operate the meter. If a single red light appears the meter is still warming up. If a single green light appears, no detectable methane gas is present. If several green lights appear, methane is present but the concentration of methane is less than 1 percent. The green lights can be counted to determine the concentration to the nearest 0.2 percent. If the green lights and one red light are visible, the concentration is 1 percent. Several red lights indicate higher concentrations which can be determined by counting the red lights. If there is a gap between the last two red lights, then the "OVER RANGE" light is on indicating that the concentration of methane exceeds 2 percent and appropriate action should be taken.

It is a great advantage that all of the above functions are performed by merely pressing the single operating button making it easy to use, especially in poor light. Furthermore, the display is easily interpreted and does not present any erratic or false indications during warm-up since the resistor $R_1$ drives the bridge into negative imbalance until the catalytic and compensating resistance elements have warmed-up. There are no mechanical parts to cause difficulty and with only a single green LED turned on for zero concentration of gas, the meter consumes a minimum of power. The unique design of the meter also permits it to operate on one 6 volt cadmium battery rather than the two required in other 12 volt meters. With only the catalytic and compensating resistance elements connected in adjacent legs of the Wheatstone bridge as in prior art meters, sufficient voltage must be available for an equal drop in potential across each element. Since approximately 3 volts are required to operate the platinum catalytic resistance element, 6 volts are required across the bridge which necessitates providing a higher voltage source such that a regulated 6 volts can be maintained With the resistor $R_1$ in parallel with the compensating element, 3 volts can be maintained across the active element while less than 6 volts are required across the bridge. In the exemplary circuit a regulated 4 volts is applied to the bridge such that only one 6 volt battery is required which significantly reduces the cost, size and weight of the meter. This is achieved while maintaining an accuracy of ±0.2 percent which is suitable for the application for which it is designed.

In addition, the disclosed gas analyzer does not have any dangerous failure modes like the digital display on some prior art analyzers discussed above. If one LED or its associated circuitry fails, the maximum error would be 0.2 percent for the scale shown. Thus the device is a safe, reliable meter for use in critical applications such as the detection of methane gas in coal mines.

Although the invention has been described with reference to a specific embodiment thereof, it is not to be limited thereby but is to be given a scope commensurate with the spirit of the following claims.

I claim as my invention:

1. A gas analyzer comprising:
a Wheatstone bridge including a catalytic resistance element in a first leg thereof exposed to the gas to be analyzed and a compensating resistance element in a second leg, said resistance elements each having an electrical resistance which increases in response to heat generated by an electric current passed therethrough, the electrical resistance of said catalytic resistance element being further increased by heat generated by combustion of the gas to be analyzed coming in contact with the heated catalytic resistance element;
an electric power supply connected to said Wheatstone bridge;
a plurality of light emitting diodes arranged to form an analog display;
means for applying electric power from said power supply to successive LEDs in the analog display in proportion to the imbalance of the Wheatstone bridge produced by the presence of the gas to be analyzed including a reference voltage generator for generating a plurality of voltages ranging in magnitude in steps from a voltage corresponding to a balanced output of the bridge up to a voltage corresponding to a predetermined imbalance, and comparison means associated with each LED in the analog display for comparing the output of the Wheatstone bridge with one of said plurality of reference voltages and for turning on the associated LED when the output of the bridge circuit exceeds the associated reference voltage; and
an impedance which is relatively temperature independent compared to the catalytic and compensating resistance elements connected in parallel with the compensating resistance element in said second leg of the Wheatstone bridge which drives the bridge circuit negative and prevents the LEDs in the analog display from illuminating until the catalytic and compensating resistance elements reach operating temperature.

2. The analyzer of claim 1 wherein the electric power supply includes a battery and a voltage regulator set to apply a preset voltage to the Wheatstone bridge, and an additional LED which is turned on when energized by a voltage above its threshold voltage and is turned off otherwise, said additional LED being connected to the voltage regulator by means which apply a voltage to the additional LED which exceeds the threshold voltage when the output of the voltage regulator is at said preset value and which falls below said threshold voltage when the voltage output of the voltage regulator drops a proportionate amount below the present value whereby said additional LED serves as a battery tester for the analyzer.

3. The analyzer of claim 2 including an electronic switch shunting said additional LED and having a control element which when energized turns on said electronic switch to shunt the additional LED, said control element being connected to the LED in the analog display associated with a balanced Wheatstone bridge whereby the additional LED is turned off when the catalytic and compensating resistance elements warm-up and generate an output for the Wheatstone bridge which turns on said LED in the analog display.

4. The gas analyzer of claim 3 including a single switch which through a single operating stroke applies power from the battery to the voltage regulator which initiates warm-up of the catalytic and compensating resistance elements, illuminates the additional LED to indicate proper voltage and provides the electric power for the warmed up catalytic and compensating resistance elements to turn on a number of successive LEDs in the analog display in proportion to the subject gas present and turn off the additional LED.

* * * * *